(12) United States Patent  (10) Patent No.: US 7,802,909 B2
Baker  (45) Date of Patent: Sep. 28, 2010

(54) MULTIFUNCTIONAL MEDICAL EXAMINATION INSTRUMENT

(75) Inventor: Jeff Baker, Orlando, FL (US)

(73) Assignee: Noble Marketing, Inc., Orlando, FL (US)

( * ) Notice: Subject to any disclaimer, the term of this patent is extended or adjusted under 35 U.S.C. 154(b) by 148 days.

(21) Appl. No.: 11/930,333

(22) Filed: Oct. 31, 2007

(65) Prior Publication Data

US 2009/0112067 A1 Apr. 30, 2009

Related U.S. Application Data

(63) Continuation-in-part of application No. 11/232,378, filed on Sep. 20, 2005, now abandoned.

(51) Int. Cl.
*A61B 1/06* (2006.01)

(52) U.S. Cl. .................................. 362/572; 362/183

(58) Field of Classification Search ............... 362/572, 362/573, 574, 183
See application file for complete search history.

(56) References Cited

U.S. PATENT DOCUMENTS

| 3,643,083 | A | * | 2/1972 | Heine | .................. 320/135 |
| 4,991,069 | A |   | 2/1991 | Tiller | |
| 6,383,133 | B1 |   | 5/2002 | Jones | |
| 6,522,534 | B1 |   | 2/2003 | Wu | |
| 6,773,192 | B1 |   | 8/2004 | Chao | |
| D497,616 | S |   | 10/2004 | Ma et al. | |
| D502,216 | S |   | 2/2005 | Chen | |
| 6,905,352 | B2 |   | 6/2005 | Chao | |
| 6,932,276 | B1 |   | 8/2005 | Liu | |
| 6,944,701 | B2 |   | 9/2005 | Yu et al. | |
| 6,979,104 | B2 | * | 12/2005 | Brass et al. | ................ 362/231 |
| 7,029,193 | B1 |   | 4/2006 | Chao | |
| D547,374 | S |   | 7/2007 | Deng | |
| 2005/0009388 | A1 |   | 1/2005 | Chao | |
| 2005/0240692 | A1 |   | 10/2005 | Li | |
| 2006/0250787 | A1 |   | 11/2006 | Ho et al. | |
| 2007/0268688 | A1 | * | 11/2007 | Chen | ......................... 362/183 |

* cited by examiner

*Primary Examiner*—Gunyoung T Lee
(74) *Attorney, Agent, or Firm*—Timothy H. Van Dyke; Beusse Wolter Sanks; Mora & Maire

(57) ABSTRACT

Disclosed herein are various embodiments of a medical instrument used for conducting eye, ear, mouth examinations of a patient. The instrument is connectable with a remote power supply. In an exemplified embodiment, instrument comprises an elongated, rigid body defining a first end and a second end, a light emitting member disposed at the first end, and an input/output connector disposed at the second end and adapted for selective connection with the remote power supply, so as to enable operation of the light emitting member free of connection with the remote power supply. The instrument may also be used for sensitivity testing of skin areas of the patent.

15 Claims, 9 Drawing Sheets

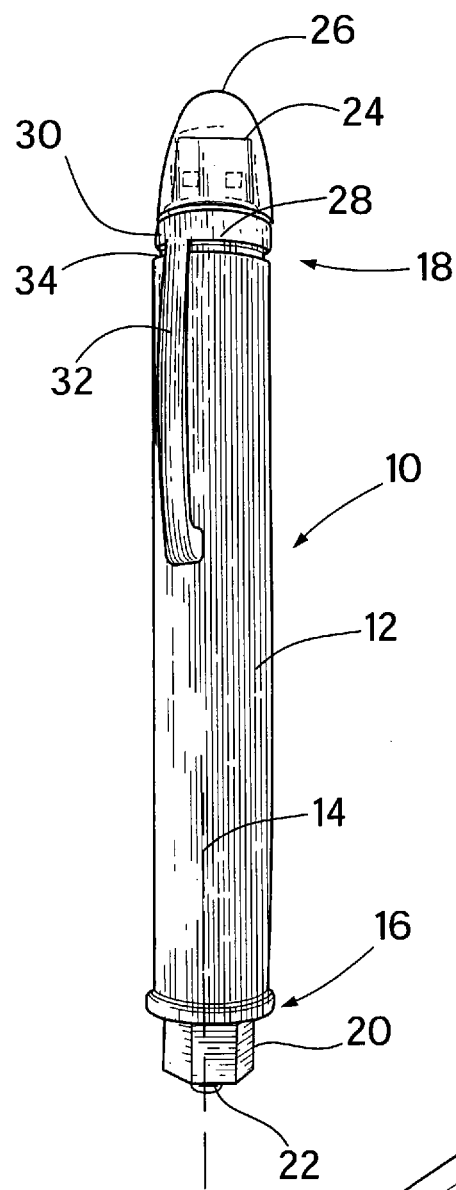
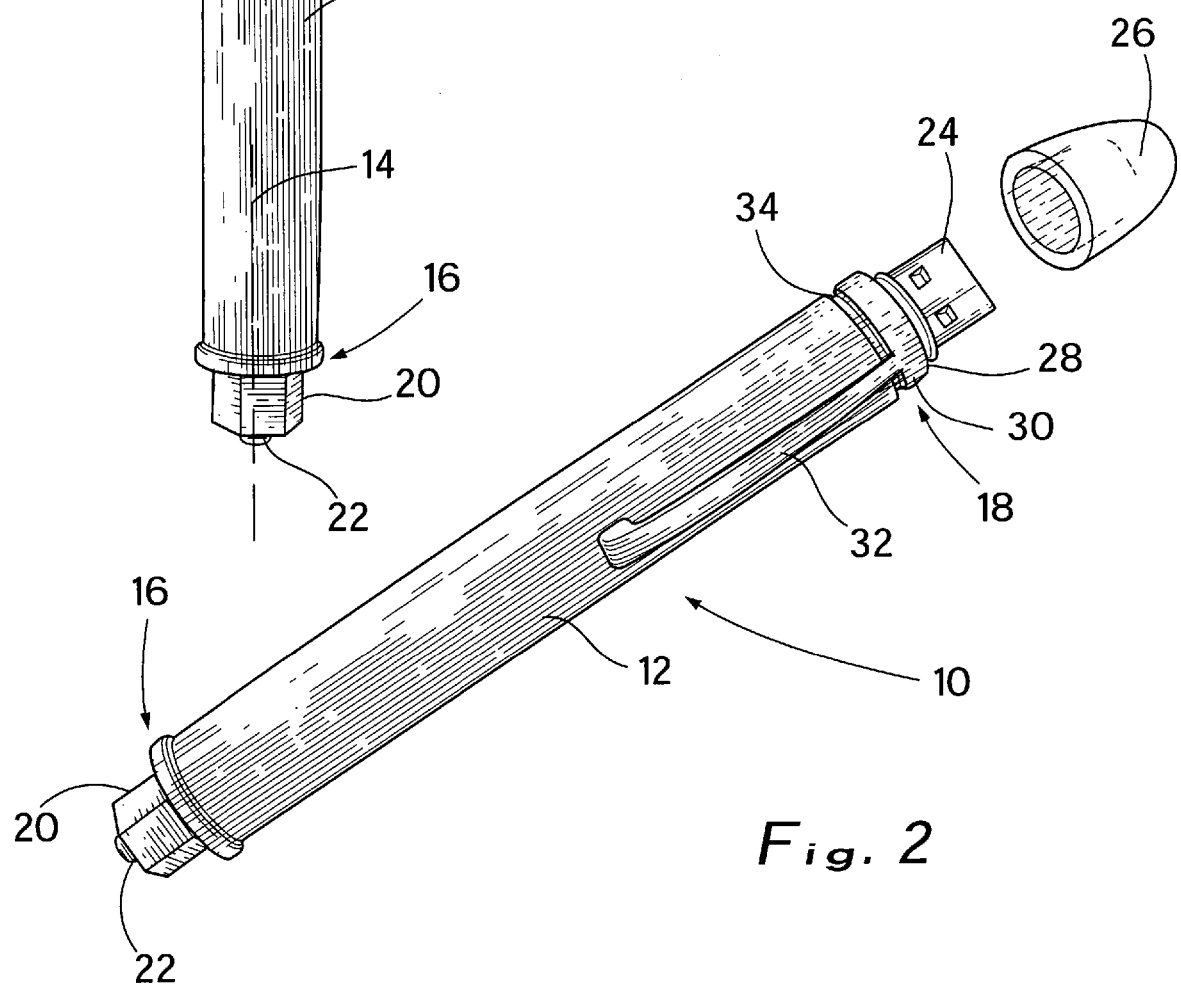
Fig. 1
Fig. 2

MULTIFUNCTIONAL MEDICAL EXAMINATION INSTRUMENT

RELATED APPLICATIONS

This application is a continuation-in-part of U.S. Ser. No. 11/232,378 filed Sep. 20, 2005 now abandoned, which is incorporated herein in its entirety.

BACKGROUND

The subject matter described herein generally relates to instruments adapted to assist in the accomplishment of certain tasks, and in exemplary fashion, to instruments which afford a desired degree of convenience when undertaking one or more tasks associated with the course of a medical examination. In addition, the instruments described herein may furthermore serve a marketing or promotional function.

Marketing products to a consumer and gaining repeat business has become more difficult as an increasing number of companies sacrifice innovation for financial stability by offering competing products having substantially similar features and specifications. Products designed to match the best product in a class often sell, but these products fail to encourage customer loyalty and repeat business because consumers fail to distinguish one product from another. Today, differentiating a product, innovating, and engaging the consumer on an emotional level are the keys to a successful marketing plan (Ealey, L. and L. Troyano-Bermudez, *The McKinsey Quarterly*, 1996 (4):62-75). Traditional "face-to-face, or "one-on-one" selling time with a consumer continues to decline in both quantity and quality. Without some constant reminder, and more particularly a reminder that draws attention to itself, the client may fail to recommend the product, or select it over a similar competing product when re-ordering.

In an effort to increase product awareness, businesses often use promotional items. The art of making and using promotional items is well established, unlike the particular manner of promotion that may be used. It is a subset of general advertising and marketing in which a physical item, at times a sample of the actual item, rather than print advertising, is provided to a consumer or a potential consumer. These items typically include calendars, pens, magnets, caps, key chains and the like. Items traditionally used are usually simple products that are only capable of marketing a product in a discreet manner. These items often provide little motivation for continued use by a consumer, thereby minimizing their effectiveness as a marketing instrument, and often, diminishing the utilitarian advantage(s) offered by the product.

It is axiomatic that in the field of advertisement/marketing, perception is often reality. Thus, a novel promotional product may make an immediate, and indelible positive first impression, whereas the presentation of an ordinary, nondescript promotional product may actually foreclose future business opportunities. When a salesperson hands out a product having an intrinsic utility and a promotional capability, that product often is a success. The most unique, practical and appealing promotional products will be those which are remembered and, consequently, will be those which lead to an increase in customer goodwill, referral and repeat business. A consumer will likely be interested in receiving an eye-catching promotional product, particularly if it has a function that commands its continued use. The most successful promotional products will be capable of establishing brand recognition by reinforcing a visual message, even when the consumer is not engaged in an activity normally associated with the product's use. For example, a consumer may be inclined to display a unique promotional product having a separate utility on his or her desk for use in various beneficial applications which include those not originally contemplated by the manufacturer. Through repeat use of the product, the consumer will be reminded of both its apparent and underlying advantages, thereby increasing the likelihood of repeat business or referrals. The more original the promotional product, the more likely it will be remembered.

Many times, products which are the most successful are marketed in channels in which certain users or intermediate distributors are instrumental to the sale of such products, for example physicians who have the authority to prescribe one pharmaceutical product over another having a similar effect. Here, lest the physician tire of the promotional product and dispose of it, a challenge exists to provide an interesting promotional product that will communicate the message of the product, and also provide a further utility in the form of decoration, amusement, and/or a specific function.

Accordingly, a need remains for promotional products that have both a marketing function and a specific utility, and that are well suited for intermediate distributors such as physicians. Physicians, many times, are likely to use promotional products in accomplishing their various tasks, and in turn, develop goodwill toward such products if they serve to assist in the achievement of one or more particular tasks.

BRIEF DESCRIPTION OF THE DRAWINGS

FIG. 1 is a perspective view of a first embodiment of the present invention.

FIG. 2 is a perspective view of the first embodiment with the cap exploded therefrom.

Figure 3:
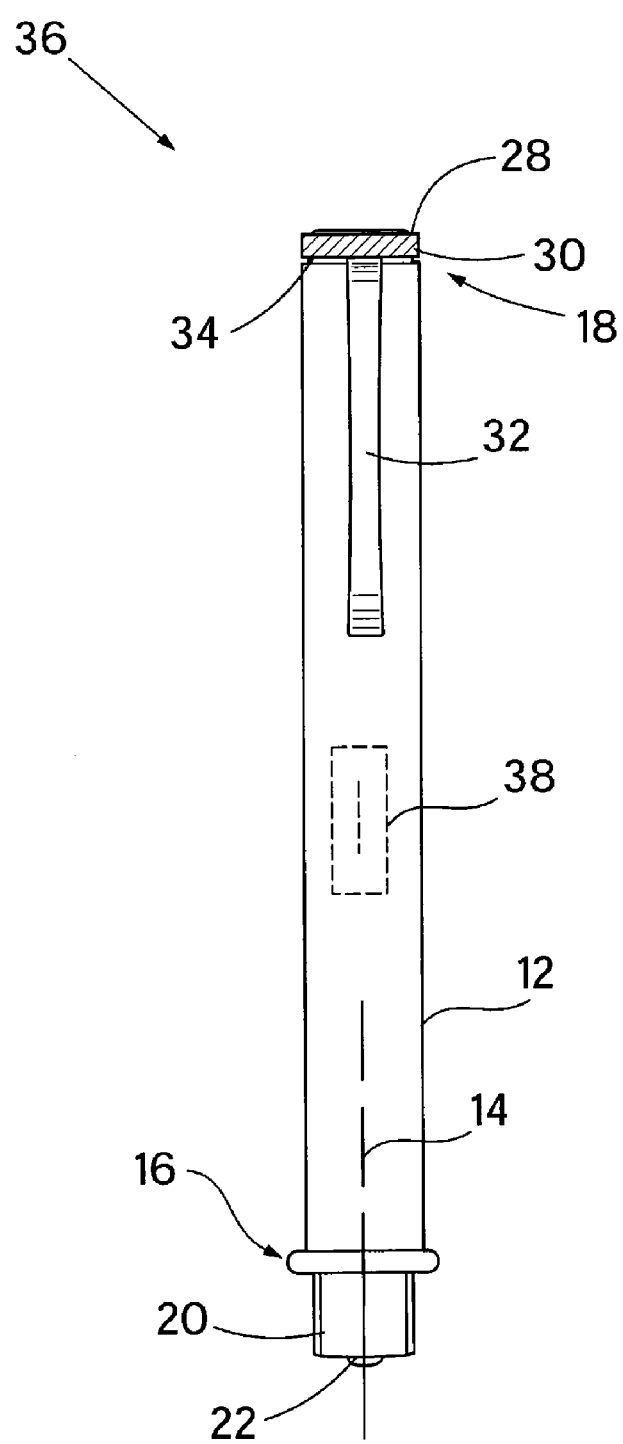
FIG. 3 is a front view of a second embodiment of the present invention.
Figure 4:
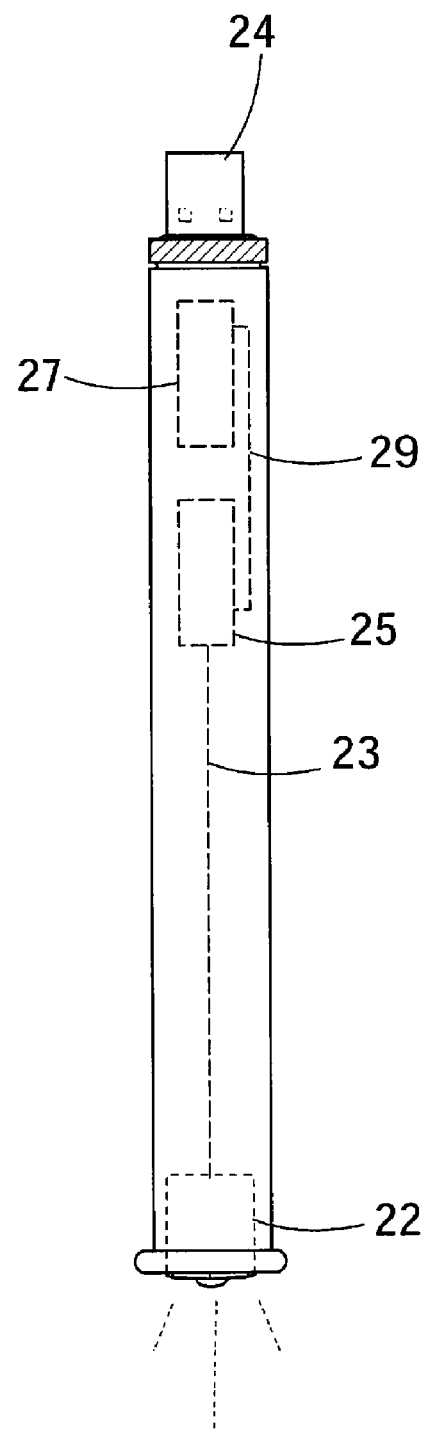
FIG. 4 is an inverted rear view of the first embodiment, showing the internal components in phantom and the cap removed therefrom.

REFERENCE NUMERALS UTILIZED IN THE DRAWING 10 instrument
12 elongated body of instrument 10
14 longitudinal axis of elongated body 12
16 first end of elongated body 12
18 second end of elongated body 12
20 cylindrical housing of instrument 10
22 light emitting member of instrument 10
23 circuitry of instrument 10
24 I/O connector of instrument 10
25 rechargeable power supply of instrument 10
26 shield of instrument 10
27 memory component of instrument 10
28 actuator of instrument 10
29 electrical conductivity components of instrument 10
30 twistable switch for actuator 28
32 fastener of instrument 10
34 ring of fastener 32
36 instrument
38 I/O connector of instrument 36
110 multifunctional medical examination instrument
112 elongated body of instrument 110
116 first end of elongated body 112
118 second end of elongated body 112
122 light emitting member of instrument 110
124 I/O connector of instrument 110
124a USB connector for I/O connector 124
125 rechargeable power supply of instrument 110
126 cap of instrument 110
128 actuator of instrument 110
130 push button switch for actuator 128
132 fastener of instrument 110
132a clip for fastener 132
140 medical examination component of instrument 110
142 otoscope attachment for medical examination component 140
144 base fitting of otoscope attachment 142
146 hollow neck of otoscope attachment 142
148 collar of otoscope attachment 142
150 head of otoscope attachment 142
152 speculum of otoscope attachment 142
154 viewing end of otoscope attachment 142
156 magnifying lens in viewing end 154
158 mirror in head 150
160 first sensitivity tester for medical examination component 140
162 longitudinal slot in clip 132a
164 pivoting structure of first sensitivity tester 160
166 flexible filament of first sensitivity tester 160
168 one end of flexible filament 164
170 second sensitivity tester for medical examination component 140
172 longitudinal area on clip 132a
174 pivoting structure of second sensitivity tester 170
176 flexible filament of second sensitivity tester 170
178 one end of flexible filament 176

DETAILED DESCRIPTION

Today, the workplace often presents tasks which are of an increasing complexity, as is the manner in which such tasks are accomplished. Those having to accomplish such tasks yearn for ways to decrease the number of steps they must undertake to achieve their successful completion. Almost always, heightened convenience over conventional means is a primary desire. Such convenience often serves as a hallmark of a product which can meet the needs of a consumer in these regards. This is especially true of those individuals serving in the medical profession where an ability to use instruments that save time, effort and expense is paramount. An example of such instruments include portable computers, cell phones and, more broadly, any instrument having an ability to be transported from place to place and whose power supply is of a rechargeable nature.

The subject matter discussed herein is best understood with reference to the FIGURES, wherein like reference numerals refer to like elements throughout.

In looking to FIGS. 1, 2, 4, 5 and 6 there is provided an instrument 10 which, it is contemplated, will increase the efficiency, and thus the convenience in carrying out one or more tasks. More specifically, it is contemplated that such tasks relate to those concerning the responsibility of medical professionals; and namely, the tasks of examination requiring a light source, and optionally, information storage and processing. As may be seen in FIG. 1, the instrument 10 comprises an elongated body 12 comprising a longitudinal axis 14 extending therethrough and defining first and second ends 16 and 18, respectively. The body 12 is, optionally, provided as rigid in its construction wherein such construction is formed from, for example, but not limited to, metal or plastic material composition, or some combination thereof.

A cylindrical housing 20 containing a light emitting member 22 is disposed at the first end 16 of the body 12, and configured so as to project light out the elongated body 12 about the longitudinal axis 14. The light emitting member 22 is provided, optionally, in the form of a conventional bulb which is "retina safe" so as to not be injurious to a patient's eye, which are to be in receipt of light therefrom during examination. It is to be understood that light emitting member 22 has associated therewith circuitry 23 that is housed within the body 12 and which is in electrical communication with a rechargeable power supply 25, such as a battery, effective to provide energy to light emitting member 22 to generate light.

An input/output ("I/O") connector 24 is mounted with the body 12 at the second end 18 thereof. The I/O connector 24 is, optionally, provided in the form of a universal serial bus ("USB") connector. I/O connectors may include, but are not limited to, I/O type connectors conventionally used to connect input and/or output devices (flash drives, keyboard, camera, mouse, printer, monitor, etc.) to a computer, including but not limited to USB connector or IE 1394 connector. The I/O connector 24 is operable, as necessary, with conventional circuitry and other electrical conductivity components 29 which are housed within the body 12 so as to enable the rechargeable power supply 25 to be recharged, and further, to enable transfer of information to and from a memory component 27. The memory component 27 may be any suitable medium for transfer, storage and/or processing of digital information, including but not limited to a memory component implemented in a conventional flash drive. It is contemplated that the I/O connector 24 will be configured for selective and operative connection with a power and information supply (not shown) such as, optionally, a desktop or laptop computer, cell phone or other such device having an ability to process information as either an input or output. Such connection is contemplated to permit the I/O connector 24 to be mated with such a supply in order to charge the rechargeable power supply 25 of the instrument 10 in order to allow its operation free of connection with the supply, and permit the storage and processing of information transferrable between the instrument 10 and the supply. In a specific embodiment, the I/O connector 24 and memory component 27 are configured in the form of a conventional USB flash drive. The USB flash drive typically consists of a controller with a USB interface and a non-volatile memory interface that is connected to one or multiple non-volatile memories (lower level or higher level of integration are possible). Hi-Speed UFDs typically use a crystal for external clock generation, a LED is typically used as optical activity indicator, possibly a write protect switch is controlling the write access and some other components are used for the remaining circuitry. Beyond this configuration, other components might be integrated depending on the functionality of the drive, such as an MP3 player, fingerprint sensor, etc.

Figures 5, 6:
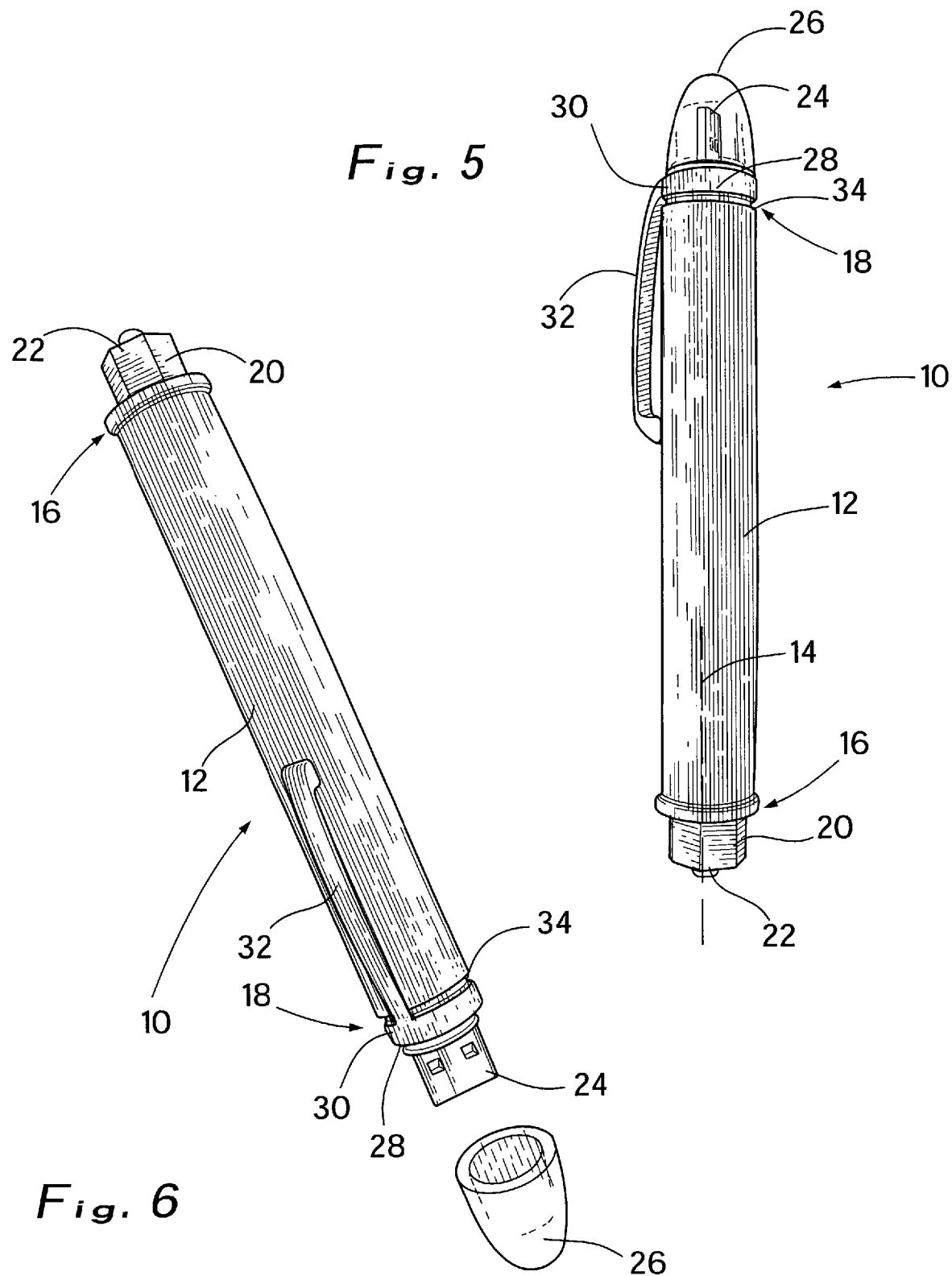
FIG. 5 is a perspective view of the first embodiment.
FIG. 6 is an inverted perspective view of the first embodiment with the cap exploded therefrom.
Figure 7:
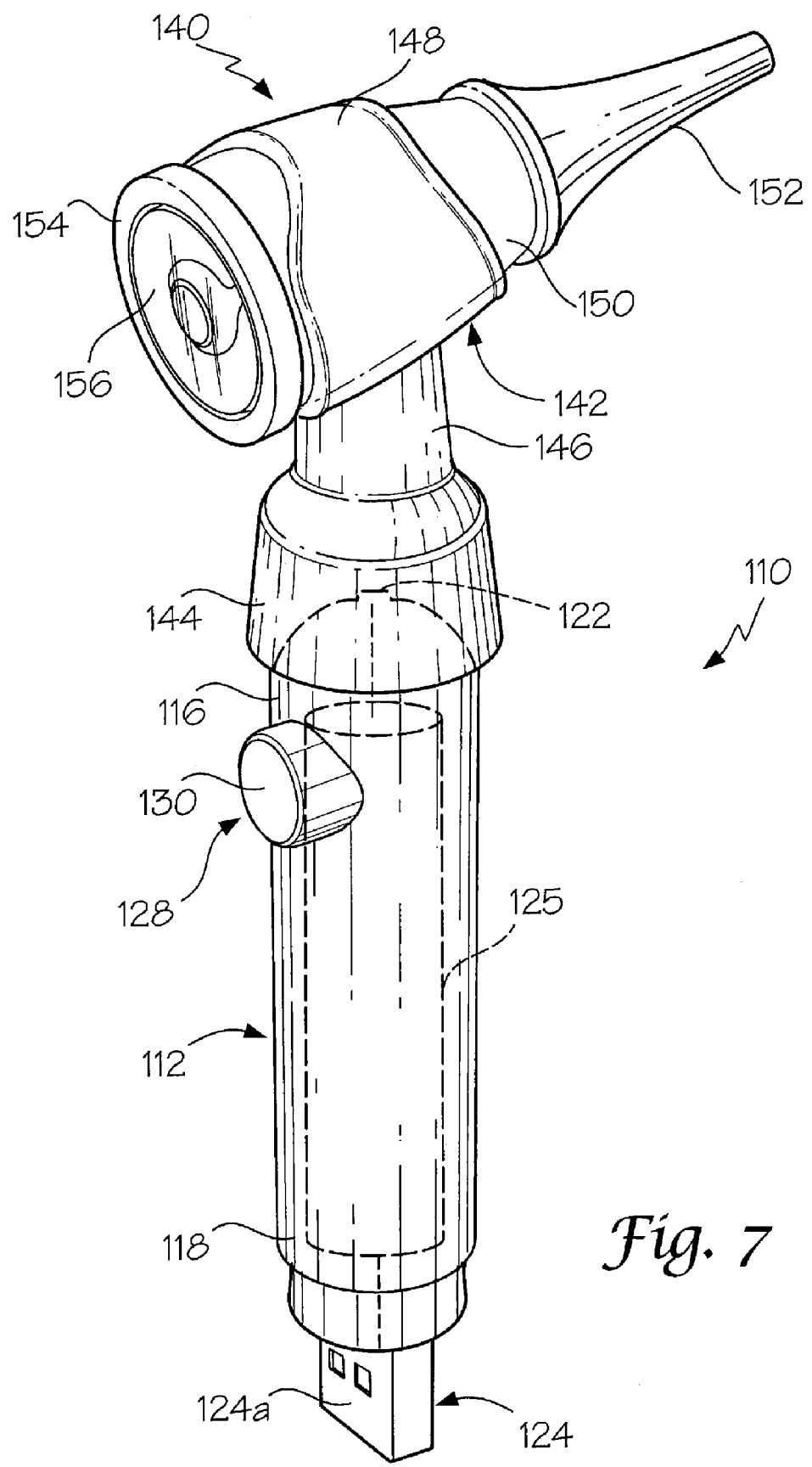
FIG. 7 is a perspective view of a third embodiment of the present invention showing a first medical examination component thereon and the cap removed therefrom.
Figure 8:
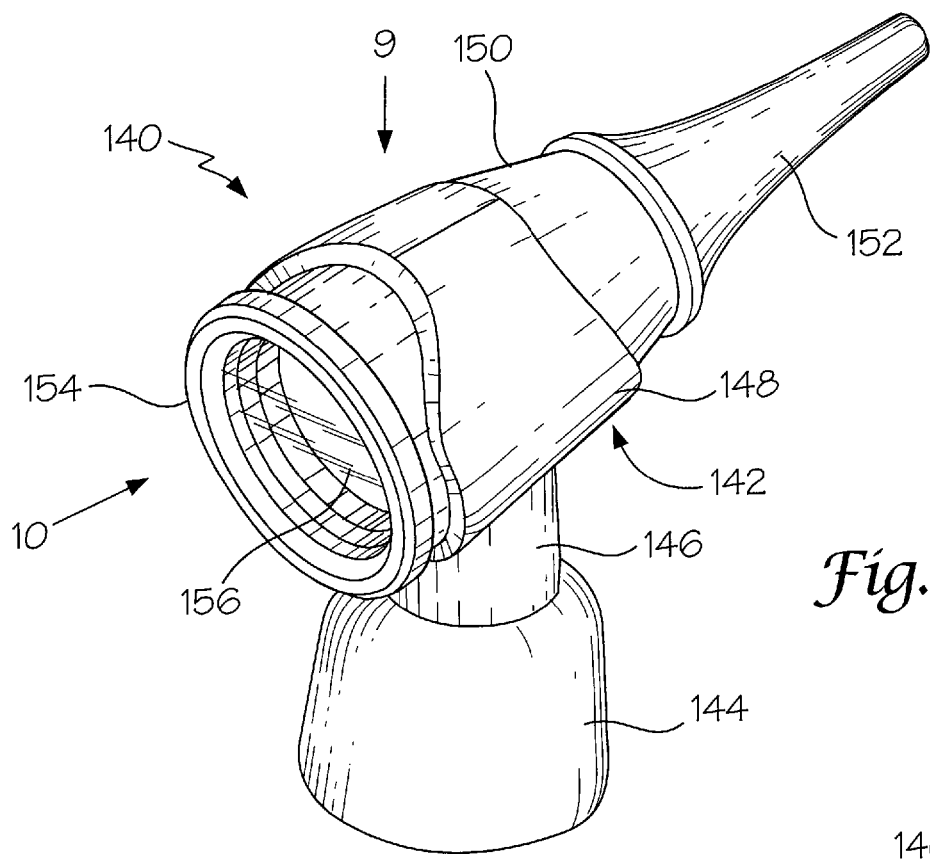
FIG. 8 is a perspective view of the first medical examination component per se.
Figure 9:
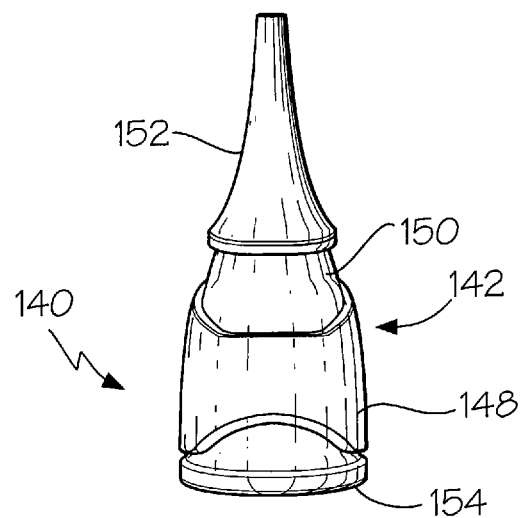
FIG. 9 is a top view taken in the direction of arrow 9 in FIG. 8.
Figure 10:
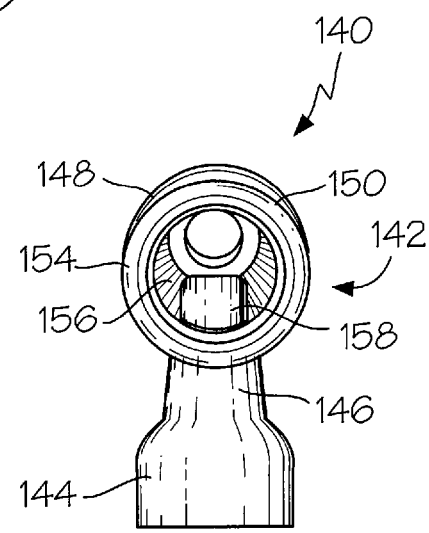
FIG. 10 is a rear view taken in the direction of arrow 10 in FIG. 8.

With continuing reference to FIGS. 1 and 2 and well as reference to FIGS. 5 and 6, it can be seen that the instrument 10 further comprises a shield 26, optionally in the form of a plastic cap, configured to fit over portions of the I/O connector 24 so as to provide protection therefor from unintended contact with objects and/or the elements. An actuator 28 is integrally formed with the second end 18 of the body 12 for controlling operation of the light emitting member 22 through its connection with a power control apparatus (not shown) housed within the body 12. The actuator 28 is, optionally, provided as a twistable switch 30 in the form of a rotatable wheel comprising ribs so as to allow beneficial gripping thereof. The actuator 28 may be integrated at any suitable portion of the instrument 10, such as, but not limited to, proximate to the first end 16 or the second end 18, wherein proximate means closer to one end than the other. A fastener 32, optionally provided as an arced metal clip, is fittingly engaged with portions of the second end 18 of the body 12 by a ring 34 which seats therewith just below the actuator 28. The fastener 32 is provided for attachment of the instrument 10 to an object including, for example, a shirt or coat pocket with which the instrument 10, as will be understood from the FIGURES, may easily fit within given its penlight-like configuration.

When looking to FIG. 3, it may be seen that it is contemplated that an instrument 36 is provided for purposes like those described in conjunction with the instrument 10. In contrast however, the instrument 36 is constructed so as to contain an I/O connector 38, optionally in the form of a USB drive, within the body 12. Further, the I/O connector 38 is adapted to be connected with portions of the body 12 such that the I/O connector 38 sits within or along the body 12 without projecting out from the body 12 when I/O connector 38 is not needed. Such a connection permits portions of the I/O connector 38 to be selectively deployable from the body 12 so as to allow a user to obtain operative connection with a chosen power and information supply, and then reengaged within the body 12 when use of the I/O connector 38 is complete. This configuration may include, but is not limited to, a hinging mechanism that enables the I/O connector 38 to pivot out from the body 12.

In another embodiment, the subject invention is directed to method of promoting a product comprising placing marketing information on the elongated body 12, or some other part of the instrument 10 as described herein. In a specific embodiment, the marketing information relates to the name of a pharmaceutical or medical instrument product that is prescribed or used by physicians, or other medical personnel. The placement of such information on the instrument 10 used by medical personnel provides a powerful and repeated marketing effect to the ultimate customer. In alternative embodiment, a part of the examination instrument 10 as describe herein is shaped and/or colored to emulate the trade dress of a pharmaceutical or a brand of a pharmaceutical or medical instrument. For example, if a pharmaceutical is produced into a unique tablet or capsule shape, and/or is comprised of a unique color or color pattern, the cap of the instrument 10 that protects the I/O connector 24 may take the same shape or color. This provides a unique reinforcement of brand recognition.

As may be appreciated by reference to the above, either of the instruments 10 or 36 is constructed so as to allow selective and easy manipulation thereof by the user, whereby such manipulation comprises an ability for the instrument 10/36 to be easily grasped, carried, oriented and powered, all in accordance with aspects of its portability serving to assist its user in the accomplishment of a desired task. FIGS. 5 and 6 represent drawings of instrument embodiment 10 as shown in FIGS. 1 and 2, inter alia.

In looking to FIGS. 7 and 11 to 15 there is provided a multifunctional medical examination instrument 110 comprising an elongated body 112 having a first end 116 and a second end 118. A light emitting member 122 is disposed at the first end 116 of the elongated body 112. A rechargeable power supply 125 is disposed within the elongated body 112. The rechargeable power supply 125 is in electrical communication with the light emitting member 112. An I/O connector 124 projects out of the second end 118 of the elongated body 112. The I/O connector 124 is in electrical communication with the rechargeable power supply 125 and adapted for operative connection with an external power supply, so as to charge the rechargeable power supply 125. At least one medical examination component 140 is coupled to the instrument 110, so that a medical task can be performed.

The I/O connector 124 is a USB connector 124a and the external power supply in a computer. The instrument 110 further comprises a fastener 132 that will retain the instrument 110 within a pocket of a garment. The fastener 132 is a clip 132a. A cap 126 is selectively t connectable to the second end 118 of the elongated body 112 to protect the USB connector 124a. An actuator 128 is mounted to the elongated body 112 for controlling operation of the light emitting member 122. The actuator 128 is a push button switch 130.

As shown in FIGS. 7 through 10, the at least one medical examination component 140 comprises an otoscope attachment 142 selectively connectable to the first end 116 of the elongated body 112 over the light emitting member 122. The otoscope attachment 142 comprises a base fitting 144 that fits over the first end 116 of the elongated body 112 and covers the light emitting member 122. A hollow neck 146 is integral with and extends up from the base fitting 144. A collar 148 is connected to top of the hollow neck 146. A head 150 is mounted within the collar 148. A speculum 152 is selectively connectable to a first end of the head 150. A viewing end 154 with a magnifying lens 156 is connected to a second end of the head 150. A mirror 158 is in the head 150 to reflect light from the light emitting member 122 through the magnifying lens 156 in the viewing end 154.

Figure 11:
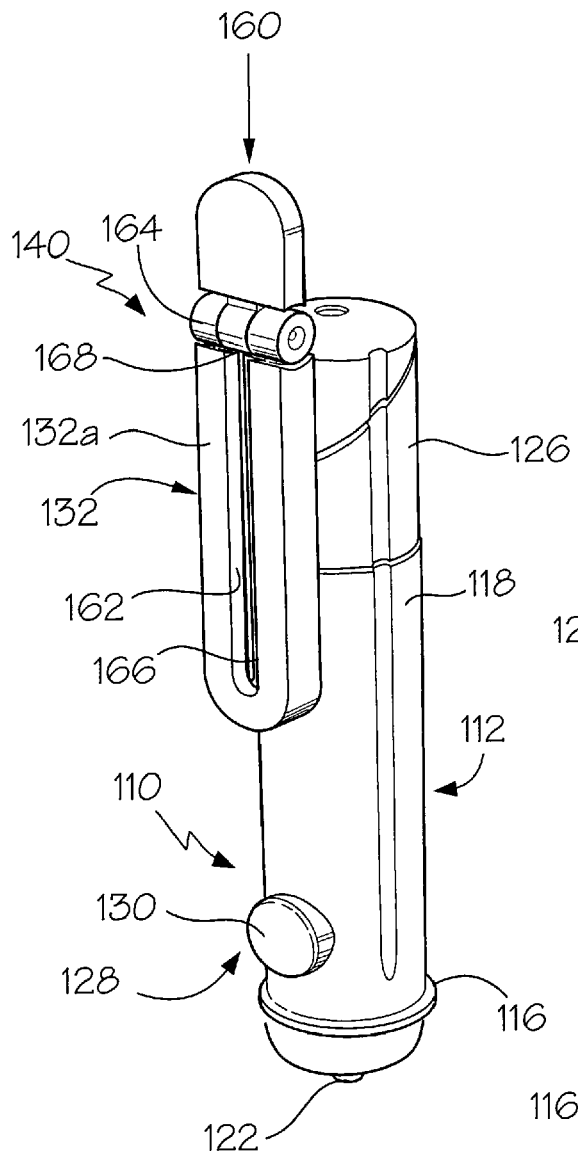
FIG. 11 is an inverted perspective view of the third embodiment showing a second medical examination component thereon.
Figure 12:
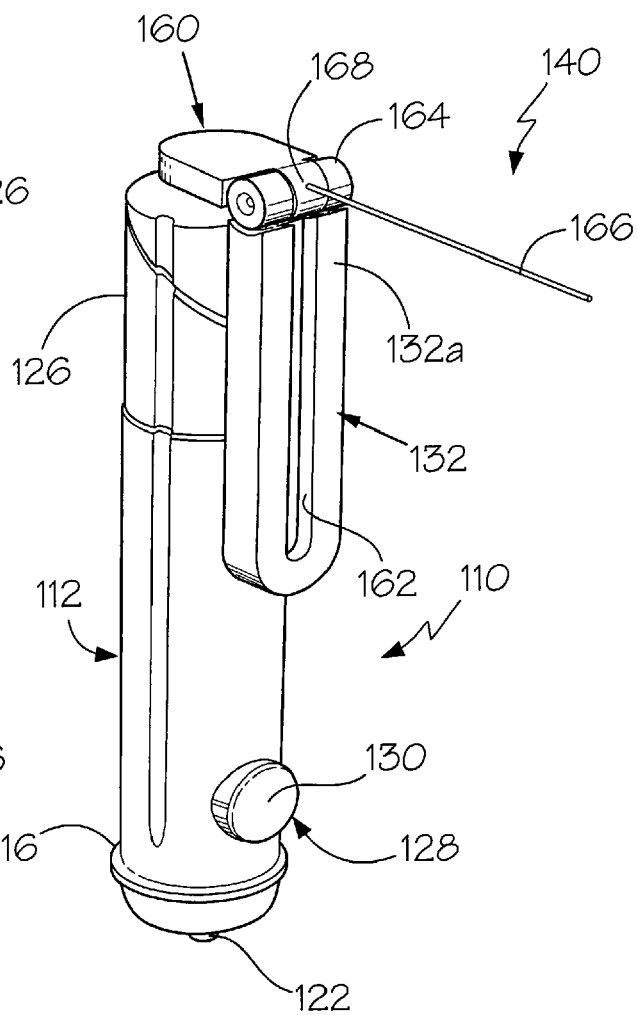
FIG. 12 is an inverted perspective view of the third embodiment showing the flexible filament of the second medical examination component in an extended useable position.

As shown in FIGS. 11 and 12 at least one medical examination component 140 comprises a sensitivity tester 160 integral with the clip 132a. The clip 132a having a longitudinal slot 162 therein is connected to the cap 126, so that the clip 132a will extend downwardly parallel along the elongated body 112. The sensitivity tester 160 comprises a pivoting structure 164 hinged to top of the clip 132a. A flexible filament 166 has one end 168 affixed to the pivoting structure 164. When the pivoting structure 164 is manually flipped down onto the top of cap 126 the flexible filament 166 will move from a stored vertical position within the longitudinal slot 162 in the clip 132a to a usable horizontal position.

Figures 13, 14, 15:
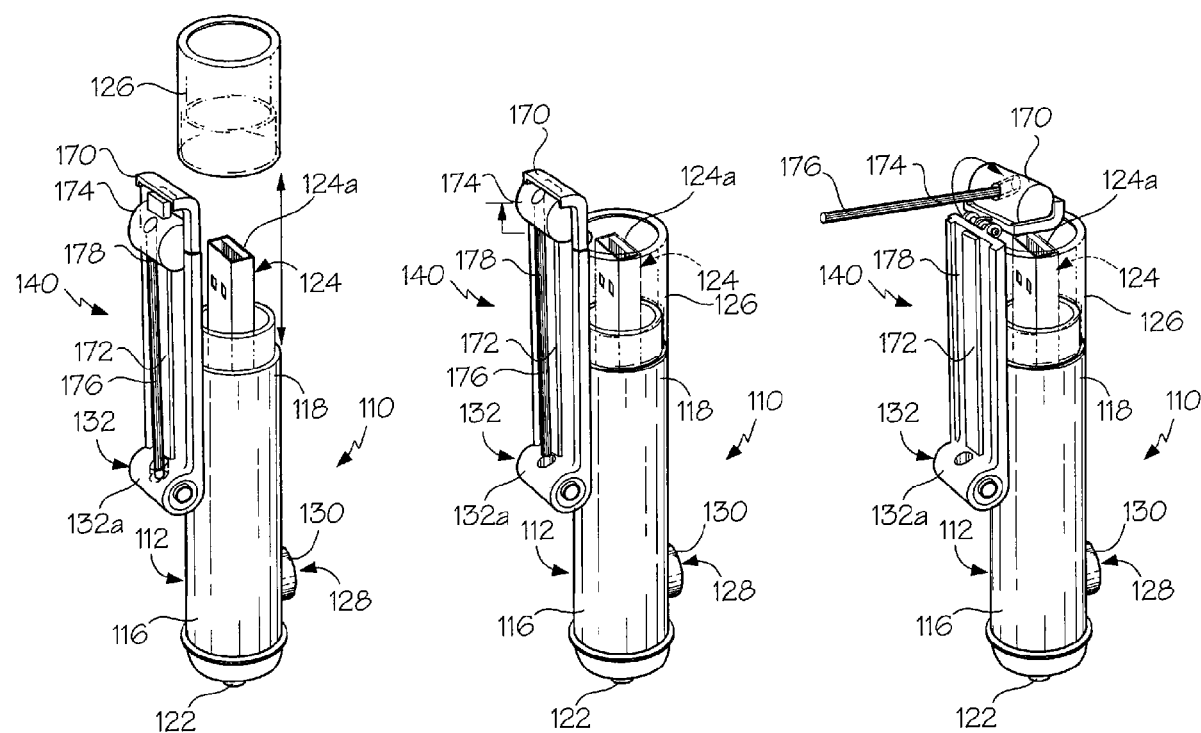
FIG. 13 is an inverted perspective view of the third embodiment showing a third medical examination component thereon and the cap exploded therefrom.
FIG. 14 is an inverted perspective view similar to FIG. 13 with the cap in place.
FIG. 15 is an inverted perspective view similar to FIG. 14 with the cap in place showing the flexible filament of the third medical examination component in an extended useable position.

As shown in FIGS. 13 through 15, the at least one medical examination component 140 comprises a sensitivity tester 170 integral with the clip 132a. The clip 132a having a longitudinal area 172 thereon is connected to the elongated body 112 at the second end 118, so that a portion of the clip 132a will extend up to top of the cap 126. The sensitivity tester 170 comprises a pivoting structure 174 hinged to top of clip 132a. A flexible filament 176 has one end 178 affixed to the pivoting structure 174. When the pivoting structure 174 is manually flipped down onto top of the cap 126, the flexible filament 176 will move from a stored vertical position within the longitudinal area 172 on the clip 132a to a usable horizontal position.

Figure 16:
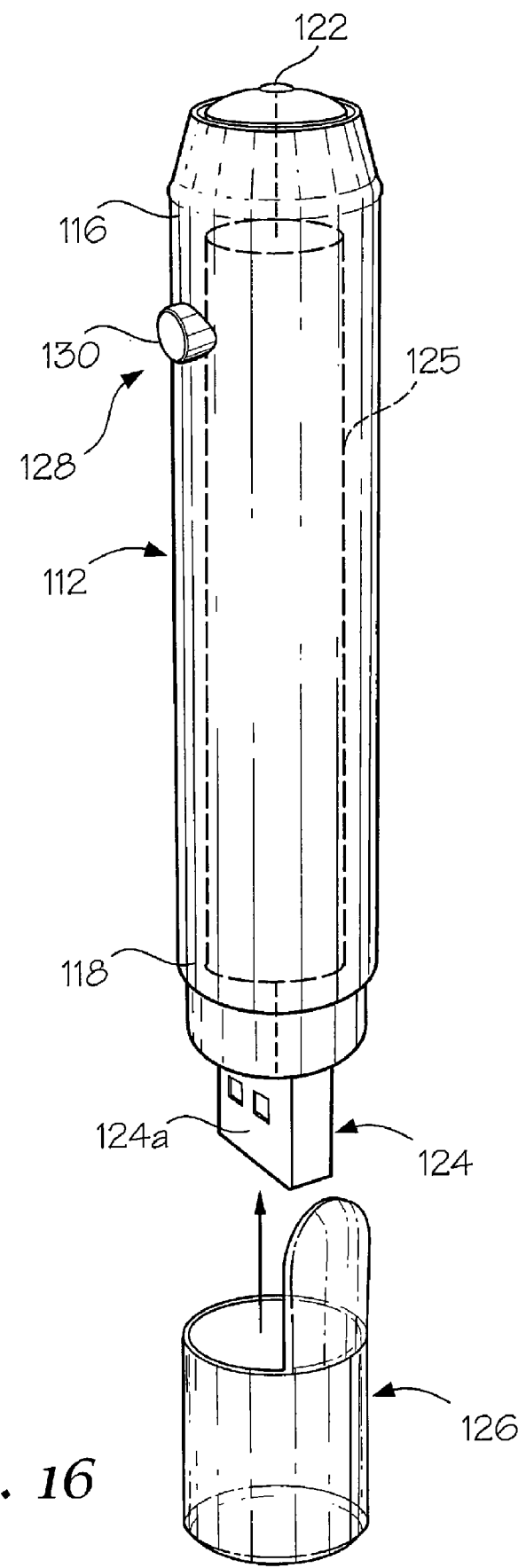
FIG. 16 shows a side perspective view of another embodiment of the present invention.
Figure 17:
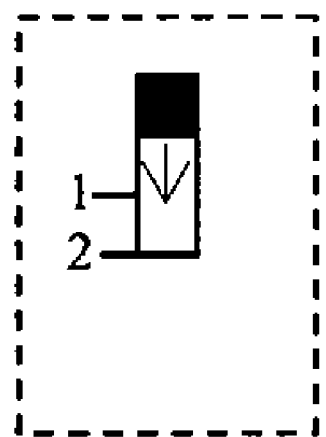
FIG. 17 shows a planar view of a light adjusting mechanism embodiment.
Figure 18:
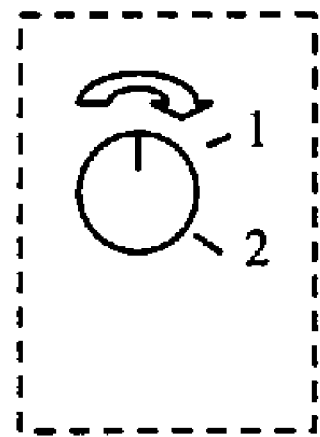
FIG. 18 shows a planar view of a light adjusting mechanism embodiment.

Another embodiment design is shown in FIG. 16. In certain embodiments, the inventors have discovered that it may be useful to have the medical instrument equipped with functionality to produce multiple intensities of light. FIG. 17 shows one mechanism for achieving more than one intensity. This is simply for illustrative purposes and those skilled in the art will understand that the inventor contemplates that there may be 2, 3, 4 5 or higher different intensities. The first setting will typically be between 100-500 lux or lower and the second setting will be higher lux than the first, typically 300-10000 lux. FIG. 18 shows another mechanism for adjusting the intensity of the light. The light adjusting mechanism will typically be implemented on the body of the instrument. In another embodiment, the light adjusting mechanism is built into the push-button switch 130 described above. According to this embodiment, the intensity will increase in a stepwise fashion upon repeated pushing of the push-button. The instrument will return to an off position upon a pre-determined number of depressions of the push-button.

In some medical situations, it will be beneficial to provide the light emitting device as fluorescence light. This will be particularly useful for conducting skin examinations. In an alternative embodiment, the light emitting member is a laser.

In other alternative embodiments, attachments to conventional otoscope kits can be adapted for use with a medical examination instrument as taught herein. For example, U.S. Pat. No. 6,282,133 is incorporated herein by reference.

In view of the foregoing, one can recognize that the subject matter herein provides a instrument meeting the needs of a consumer with heightened convenience in accomplishing any one or more certain tasks relative to the functions as already described. In providing such convenience, value is provided to the consumer insofar as the time, effort and expense associated with accomplishing a particular task is reduced; as such, is a value which, it is to be understood, is not to be subordinated by the particular utility offered by the instrument itself.

It is to be noted that the FIGURES depicting the subject matter herein are representative of that subject matter as it has been described and are not meant to limit the range of possible configurations. Those skilled in the art will appreciate that the scope of this subject matter should be measured by the claims appended hereto, and not merely by the specific representations exemplified herein.

What is claimed is:

1. A multifunctional medical examination instrument comprising:
   (a) an elongated body having a first end and a second end;
   (b) a light emitting member disposed at said first end of said elongated body;
   (c) a rechargeable power supply disposed within said elongated body, said rechargeable power supply in electrical communication with said light emitting member;
   (d) an input/output (I/O) connector projecting out of said second end of said elongated body, said I/O connector in electrical communication with said rechargeable power supply and adapted for operative connection with an external power supply, so as to charge said rechargeable power supply; and
   (e) at least one medical examination component coupled to said instrument; wherein said I/O connector is a universal serial bus (USB) connector and the external power supply is a computer.

2. The instrument as recited in claim 1, further comprising a fastener that will retain said instrument within a pocket of a garment.

3. The instrument as recited in claim 2, wherein said fastener is a clip.

4. The instrument as recited in claim 3, further comprising a cap selectively connectable to said second end of said elongated body to protect said USB connector.

5. The instrument as recited in claim 4, further comprising an actuator mounted to said elongated body for controlling operation of said light emitting member.

6. The instrument as recited in claim 5, wherein said actuator is a push button switch.

7. The instrument as recited in claim 1, wherein said at least one medical examination component comprises an otoscope attachment selectively connectable to said first end of said elongated body over said light emitting member.

8. The instrument as recited in claim 4, wherein said at least one medical examination component comprises a sensitivity tester integral with said clip, wherein said clip having a longitudinal slot therein is connected to said cap, so that said clip will extend downwardly parallel along said elongated body.

9. The instrument as recited in claim 4, wherein said at least one medical examination component comprises a sensitivity tester integral with said clip, wherein said clip having a longitudinal area thereon is connected to said elongated body at said second end, so that a portion of said clip will extend up to top of said cap.

10. The instrument as recited in claim 9, wherein said sensitivity tester comprises:
    (a) a pivoting structure hinged to top of said clip; and
    (b) a flexible filament having one end affixed to said pivoting structure, so that when said pivoting structure is manually flipped down onto top of said cap, said flexible filament will move from a stored vertical position within said longitudinal area on said clip to a usable horizontal position.

11. The instrument as recited in claim 4, wherein said at least one medical examination component comprises a sensitivity tester integral with said clip, wherein said clip having a longitudinal area thereon is connected to said elongated body at said second end, so that a portion of said clip will extend up to top of said cap.

12. The instrument as recited in claim 11, wherein said sensitivity tester comprises:

(a) a pivoting structure hinged to top of said clip; and (b) a flexible filament having one end affixed to said pivoting structure, so that when said pivoting structure is manually flipped down onto top of said cap, said flexible filament will move from a stored vertical position within said longitudinal area on said clip to a usable horizontal position.

13. The instrument as recited in claim 7, wherein said otoscope attachment comprises:

(a) a base fitting that fits over said first end of said elongated body and covers said light emitting member;

(b) a hollow neck integral with and extending up from said base fitting;

(c) a collar connected to top of said hollow neck;

(d) a head mounted within said collar;

(e) a speculum selectively connectable to a first end of said head;

(f) a viewing end with a magnifying lens connected to a second end of said head; and (g) a mirror in said head to reflect light from said light emitting member through said magnifying lens in said viewing end.

14. The instrument as recited in claim 8, wherein said sensitivity tester comprises:

(a) a pivoting structure hinged to top of said clip; and (b) a flexible filament having one end affixed to said pivoting structure, so that when said pivoting structure is manually flipped down onto the top of said cap said flexible filament will move from a stored vertical position within said longitudinal slot in said clip to a usable horizontal position.

15. The instrument as recited in claim 1, wherein said light emitting member emits fluorescent light.

* * * * *